United States Patent
Matsuo (10) Patent No.: US 9,078,736 B2
(45) Date of Patent: Jul. 14, 2015

(54) INSTRUMENT FOR PREVENTING OR TREATING HEMORRHOIDS, AND METHOD FOR PREVENTING OR TREATING HEMORRHOIDS

(75) Inventor: Atsushi Matsuo, Sanda (JP)

(73) Assignee: Kobayashi Pharmaceutical Co., Ltd., Osaka-shi (JP)

( * ) Notice: Subject to any disclaimer, the term of this patent is extended or adjusted under 35 U.S.C. 154(b) by 452 days.

(21) Appl. No.: 12/735,306

(22) PCT Filed: Dec. 4, 2009

(86) PCT No.: PCT/JP2009/070430
§ 371 (c)(1),
(2), (4) Date: Mar. 8, 2011

(87) PCT Pub. No.: WO2011/001553
PCT Pub. Date: Jan. 6, 2011

(65) Prior Publication Data
US 2011/0152985 A1 Jun. 23, 2011

(30) Foreign Application Priority Data
Jul. 2, 2009 (JP) .................................. 2009-157793

(51) Int. Cl.
*A61F 7/08* (2006.01)
*A61F 7/00* (2006.01)
*A61F 7/03* (2006.01)
*A61F 7/02* (2006.01)

(52) U.S. Cl.
CPC ......... *A61F 7/034* (2013.01); *A61F 2007/0027* (2013.01); *A61F 2007/0226* (2013.01); *A61F 2007/0236* (2013.01); *A61F 2007/0244* (2013.01)

(58) Field of Classification Search
CPC ............ A61F 7/034; A61F 2007/0027; A61F 2007/0244; A61F 2007/0236; A61F 2007/0226
USPC ..................................................... 601/96, 108
See application file for complete search history.

(56) References Cited

U.S. PATENT DOCUMENTS

| 4,926,845 | A | * | 5/1990 | Harris | 602/19 |
| 5,879,378 | A | * | 3/1999 | Usui | 607/96 |
| 2006/0101558 | A1 | * | 5/2006 | Coleman et al. | 2/400 |
| 2006/0173519 | A1 | * | 8/2006 | Matsuo et al. | 607/108 |
| 2009/0177135 | A1 | * | 7/2009 | Rogers et al. | 602/54 |

FOREIGN PATENT DOCUMENTS

| CN | 2167705 Y | 6/1994 |
| JP | 36-93 | 1/1961 |
| JP | 56-66311 | 6/1981 |

(Continued)

*Primary Examiner* — Michael Peffley
*Assistant Examiner* — Daniel Fowler
(74) *Attorney, Agent, or Firm* — Locke Lord LLP

(57) ABSTRACT

The present invention provides an instrument for preventing and treating hemorrhoids, which enables easy attachment to the body, ensures comfort in use, and effectively prevents and treats hemorrhoids.

An instrument for preventing or treating hemorrhoids according to the present invention is adhered to a patient's back in contact with the sacrum and/or the skin in its periphery either directly to the skin or indirectly through clothing, the instrument including: a container having air permeability, and a heat generating material that generates heat by oxidation upon contact with air and is contained in the container.

4 Claims, 3 Drawing Sheets

(a)

(b)

(56) References Cited

FOREIGN PATENT DOCUMENTS

| | | |
|---|---|---|
| JP | 58-43100 | 2/1982 |
| JP | 04-176456 A | 6/1992 |
| JP | 8-336554 A | 12/1996 |
| JP | 4215327 | 7/2000 |
| JP | 2001-137274 A | 5/2001 |
| JP | 2003-190202 A | 7/2003 |

* cited by examiner

INSTRUMENT FOR PREVENTING OR TREATING HEMORRHOIDS, AND METHOD FOR PREVENTING OR TREATING HEMORRHOIDS

CROSS-REFERENCE TO RELATED APPLICATIONS

This application is a national stage application of, and claims priority to, International Application No. PCT/JP2009/070430 filed 04 Dec. 2009, and also claims priority to Japanese Patent Application no. 2009-157793, filed 02 Jul. 2009.

TECHNICAL FIELD

The present invention relates to an instrument for preventing or treating hemorrhoids, and a method for preventing or treating hemorrhoids.

BACKGROUND ART

Patent Literature 1 discloses an example of an instrument for treating hemorrhoids. This treatment instrument comprises a tubular main unit formed of soft plastic; and a chemical heat-generation unit contained in the main unit. When used, air is introduced into the treatment instrument to heat the heat-generation unit, and the treatment instrument is inserted in the anus of the patient. As a result, the hemorrhoid area, i.e., the vicinity of anus is warmed, thereby relieving the symptom of hemorrhoids.

PRIOR ART DOCUMENT

Patent Literature

[Patent Literature 1] Japanese Unexamined Patent Publication No. 1983-43100

SUMMARY OF INVENTION

Technical Problem

However, the above treatment instrument requires the user to insert the instrument body into the anus, and such insertion is difficult for some patients. Moreover, after the insertion, the treatment instrument stays inside the user's body, and the user may experience discomfort until they get used to the sensation of a foreign object inside their body. The present invention was made in view of the above problem, and provides an instrument for effectively preventing or treating hemorrhoids. This instrument can be easily attached to the body and ensures comfort in use. The present invention also provides a method for preventing or treating hemorrhoids.

Solution to Problem

The present invention provides an instrument for preventing or treating hemorrhoids, which is adhered to the skin over the sacrum and/or its periphery either directly to the skin or indirectly through clothing. The treatment instrument comprises a container having air permeability, and a heat generating material that generates heat by oxidation upon contact with air and is contained in the container.

Such a structure allows the treatment instrument heated by the heat generating material to come in contact with the sacrum and the peripheral area thereof. This improves the circulation of the blood in the entire pelvis, thereby relieving the symptom of hemorrhoids, particularly external hemorrhoids and internal hemorrhoids. More specifically, the expected effects of the heat given by the treatment instrument include relief of pain and itchiness caused by hemorrhoids and also reduction of hemorrhoids. Further, since the generated heat also warms the peripheral area of the sacrum, it may also have an effect of relieving constipation, thereby preventing the discharge of hard feces. This can facilitate recovery from hemorrhoids. As such, in view of the drawbacks of the conventional technique of inserting a treatment instrument into the patient's body, the present invention achieves a method of relieving the symptoms of hemorrhoids by bringing a treatment instrument into contact with the skin over the sacrum and/or its periphery either directly or indirectly. With such an instrument structure, the present invention has advantageous easy attachment to the body and comfort in use. Accordingly, the present invention is useful for the treatment of hemorrhoids including internal hemorrhoids and external hemorrhoids, or for the prevention of hemorrhoids.

The instrument for preventing or treating hemorrhoids of the present invention may be brought into contact with patient's skin in various embodiments. More specifically, the treatment instrument can be directly adhered to the skin. Otherwise, the instrument can be indirectly brought into contact with the skin through clothing; that is, the skin comes undermost, followed by clothing and then the treatment instrument is placed on top. Alternatively, the treatment instrument can be brought into contact with the skin after the treatment instrument is adhered to clothing; that is, the treatment instrument is placed between the skin and the clothing.

The instrument for preventing or treating hemorrhoids of the present invention may be structured such that the area of the container in a plan view is in a range of from 28 to 143 $cm^2$ based on the following reasons. If the area is less than 28 $cm^2$, it is not possible to warm the entire pelvis, and the instrument thereby fails to relieve hemorrhoids. On the other hand, if the area is more than 143 $cm^2$, the sensible temperature becomes too high, exceeding an appropriate range. In terms of feel of use, a preferable instrument size is less than 117 $cm^2$. An instrument of this size will not be excessively bulky and will not cause unintended detachment from the body, thereby ensuring improved comfort in use.

The instrument for preventing or treating hemorrhoids of the present invention may be structured such that the air permeability of the container is in a range of from 214 to 413 $g/m^2/day$. By setting the air permeability to 214 $g/m^2/day$ or greater, the user more easily feels warmth. By limiting the air permeability to 422 $g/m^2/day$ or less, the temperature of the portion in contact with the body will not excessively increase.

The instrument for preventing or treating hemorrhoids of the present invention may be structured so that the container has a rectangular shape in a plan view, with a substantially triangle-shaped projecting portion on one end. Because the lower end of the sacrum also has a tapered shape, the container can fit well into the sacrum by meeting the projecting portion of the container with the lower end of the sacrum. As a result, the sacrum can be more easily heated, thereby more effectively heating the entire pelvis and more effectively relieving hemorrhoids.

The method for preventing or treating hemorrhoids of the present invention comprises a step of bringing the above-described instrument into contact with the sacrum and the skin in its periphery of a hemorrhoid patient or a user trying to prevent hemorrhoids, either directly to the skin or indirectly through clothing. The method for preventing or treating hemorrhoids of the present invention has various embodiments to bring the treatment instrument into contact with skin. More specifically, the treatment instrument can be directly adhered to the skin, or the treatment instrument can be brought into contact with the skin indirectly through clothing; that is, the skin comes undermost, followed by clothing, and then the treatment instrument is placed on top. Alternatively, the treatment instrument can be brought into contact with the skin after it is adhered to the clothing; that is, the treatment instrument is placed between the skin and the clothing.

The method for preventing or treating hemorrhoids may be arranged so that the area of the container in a plan view is in a range of from 28 to 143 cm$^2$.

The method for preventing or treating hemorrhoids may be arranged so that the air permeability of the container is in a range of from 214 to 413 g/m$^2$/day.

The method for preventing or treating hemorrhoids may be arranged so that the container has a rectangular shape in a plan view, with a substantially-triangle projecting portion on one end.

The present invention further relates to the use of a heat generating instrument comprising an air-permeable container and a heat generating material that generates heat by oxidation upon contact with air and is contained in the air-permeable container, for producing an instrument for preventing or treating hemorrhoids.

Advantageous Effects of Invention

The present invention enables the treatment instrument to be easily attached to the body and ensures comfort in use. The present invention also effectively prevents and treats hemorrhoids.

DESCRIPTION OF EMBODIMENTS

Figure 1:
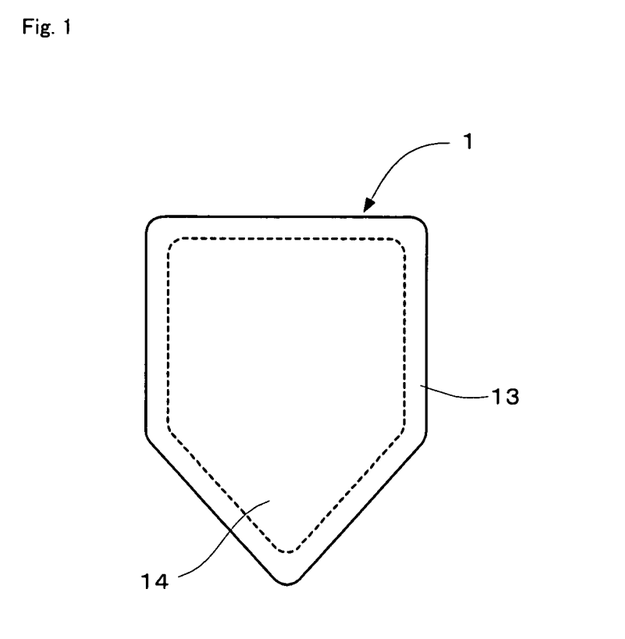
FIG. 1 A plan view illustrating one embodiment of a treatment instrument according to the present invention.
Figure 2:
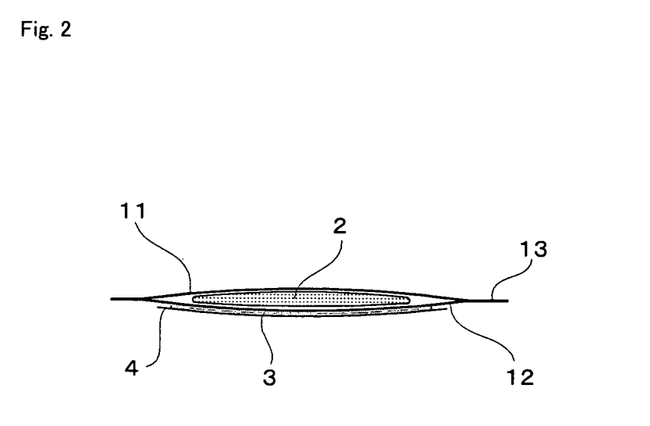
FIG. 2 A cross-sectional view of the treatment instrument of FIG. 1.

One embodiment of the treatment instrument of the present invention is described below in reference to the drawings. FIG. 1 is a plan view illustrating one embodiment of a treatment instrument according to the present invention. FIG. 2 is a cross-sectional view of the same treatment instrument.

As shown in FIG. 1, the instrument for preventing or treating hemorrhoids has a pentagon shape, and comprises a flat and air-permeable container 1; and a heat generating material 2 to be contained in the container 1, the heat generating material 2 generating heat by oxidation upon contact with air. As shown in FIG. 2, an adhesive 3 can be applied on the rear surface of the container 1. Through the adhesive 3, the container 1 can be attached to the user's body directly to skin or indirectly through clothing. When the container 1 has the adhesive 3 on its rear surface, the adhesive 3 is covered with a backing film or a backing sheet 4 that is peeled off before adhering the instrument to the user. Further, before use, the treatment instrument can be contained in an air-tight outer bag, which prevents the treatment instrument from contacting the air, thereby preventing heat generation before use. The following explains the components of the treatment instrument.

Container

The container 1 is shaped like a flat bag. At least a part of the container 1 has small or micro air holes which make the container 1 air-permeable. For example, as shown in FIG. 2, the container 1 may be structured so that the front sheet 11 provided on the front surface of the container 1 is air-permeable and the rear sheet 12 provided on the rear surface of the container 1 is not air-permeable. In this case, the adhesive 3 is applied to the rear sheet 12. The container 1 has an edge 13 that is sealed by a heat-seal, an adhesive, or the like; thereby, the front sheet 11 is adhered to the rear sheet 12 to form a bag shape having a space inside. The container 1 may be structured so that both of the front and rear sheets 11 and 12 are air-permeable, or that one of the sheets is partially air-permeable, and the rest of the container 1 is not air-permeable.

The non-air-permeable side is formed of a general non-air-permeable film or a non-air-permeable sheet used as the outer bag of a disposable warmer or the like. A single or multi-layered film or sheet can be used, as required, in combination with a woven or nonwoven fabric. Suitable resins for the film include various thermoplastic synthetic resins, such as polyethylene, polypropylene, polyester, polyamide, polyvinyl alcohol, polyvinyl chloride, polyvinylidene chloride, polyurethane, polystyrene, ethylene-vinyl acetate copolymer, polycarbonate, rubber hydrochloride and the like. These resins may be used solely or in combination. Polyethylene is particularly preferable.

An adhesive may be applied to the non-air-permeable side. Examples of the adhesives include acrylic resins and rubber resins adherable to skin and clothing. These resins can be used solely or in combination. The adhesive layer is preferably covered with a backing sheet before use. Examples of suitable materials for the backing sheet include polyethylene, paper, silicone, polypropylene, and polyethylene terephthalate.

The air-permeable side is formed of a film or sheet that is entirely permeable to air. Generally, a single or multi-layered porous film or sheet is used for the air-permeable side, solely or in combination with a woven or nonwoven fabric or the like.

Generally, thermoplastic synthetic resins or the like are suitable for a material of the film. Examples of the thermoplastic synthetic resins include polyethylene, polypropylene, polyester, polyamide, polyvinyl alcohol, polyvinyl chloride, polyvinylidene chloride, polyurethane, polystyrene, ethylene-vinyl acetate copolymer, polycarbonate, and rubber hydrochloride. These resins may be used solely or in combination. Polyethylene is particularly preferable.

Suitable films for the air-permeable film include oriented films, preferably oriented porous films, or sheets containing the porous films. Oriented porous films generally contain inorganic fillers such as calcium carbonate. The air permeability of these films is formed by pores formed by orientation of the film. Therefore, the air permeability can be controlled by controlling the pore diameter. Preferable examples of air-permeable films include an olefin-based (polyethylene-based) oriented porous lamination film, and a composite sheet of this film and a nonwoven fabric.

Film lamination is generally performed by, but not limited to, any known lamination technologies, such as thermal bonding, or lamination using hot-melt adhesives or acrylic or urethane-based adhesives. The sheet layers may be entirely combined, or partially combined to ensure sheet flexibility.

Suitable nonwoven fabrics to be used for film lamination include synthetic fibers such as nylon, vinylon, polyester, rayon, acetate, acryl, polyethylene, polypropylene, and polyvinyl chloride; and natural fibers such as cotton, hemp, and silk.

The container 1 may have a shape other than a pentagon, such as a rectangle, circle, ellipse, tongue shape, and heart shape. However, the pentagon container shown in FIG. 1 has an advantage such that the triangle projecting portion 14 on the lower end allows the treatment instrument to fit the shape of the sacrum, thereby facilitating the effect of relieving hemorrhoids. The area of the container 1 in a plan view is preferably in a range of from 28 to 143 cm², more preferably from 45 to 124 cm², particularly preferably from 45 to 117 cm². If the area is less than 28 cm², it is not possible to warm the entire pelvis, and the effect of relieving hemorrhoids is not ensured. If the area is greater than 143 cm², the sensible temperature becomes too high, exceeding an appropriate range. In terms of feel of use, the area of the container is preferably less than 117 cm². An instrument of this size will not be excessively bulky and will not unintentionally detach from the body, thereby ensuring improved comfort in use.

The thickness of the container 1 is preferably in a range of from 1 to 15 mm, more preferably 2 to 8 mm, in terms of fitting the treatment instrument to the body and preventing it from hindering the movement of the joints. The container 1 may have a uniform thickness, or an irregular thickness to vary the user's feeling of pressure.

Figure 3:
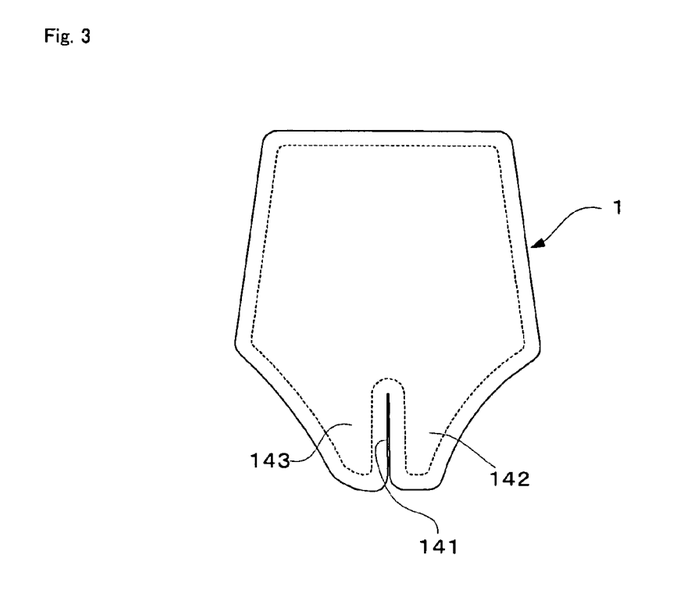
FIG. 3 A plan view illustrating another example of a treatment instrument according to the present invention.

Further, as shown in FIG. 3, the projecting portion 14 in the lower end of the container 1 may be provided with a slit 141 so that the projecting portion 14 is divided into two portions 142 and 143. The right and left portions 142 and 143 of the projecting portion 14 will individually move along with the movements of the right and left legs of the user when the treatment instrument is attached to the user's body. This prevents easy detachment of the treatment instrument from the body.

The air permeability level of the container 1 is determined so that the temperature of the portion in contact with the body will not exceed 42° C. which may cause a low temperature burn. Specifically, the air permeability of the container 1 is preferably in a range of from 214 to 413 g/m²/day, more preferably 234 to 390 g/m²/day, particularly preferably 274 to 390 g/m²/day, based on the water vapor transmission rate measured by method A (humidity sensor method) defined by JIS K7129. If the water vapor transmission rate is greater than 413 g/m²/day, the heat generating material 2 will be excessively heated. If the water vapor transmission rate is less than 214 g/m²/day, the heat generating material 2 may not be sufficiently heated.

Heat Generating Material

The heat generating material 2 generates heat by oxidation in the presence of air. Various known heat generating materials may be used. For example, the heat generating material may contain, but is not limited to, metal powder such as iron powder, activated carbon, water, a water retention agent (wood flour, vermiculite, diatomous earth, perlite, silica gel, alumina, water-absorbing resin, and the like), salt and the like. It is preferable that the heat generating material 2 is dispersed in the container 1 in a basic weight of 0.1 to 1 g per 10 mm² so as to provide uniform and gentle heat. The composition and amount of the heat generating material 2 are determined so that the temperature of the portion in contact with the body will not exceed 42° C. which may cause a low temperature burn. For example, the container 1 may contain 5 to 30 g of the heat generating material 2. Further, the composition and amount of the heat generating material 2 are preferably determined so that the degree of heat-generation per unit area is at least 45 cal/cm². The heat-generation degree depends on the iron content, and can be calculated according to the following equation using the iron content measured by the method defined by JIS M8212.

$$Fe + 3/4 O_2 + 3/2 H_2O \rightarrow Fe(OH)_3 + 98.2 \text{ kcal}$$

Further, the temperatures of the heat generating material 2 and the container 1 are determined as follows. When the highest temperature of the treatment instrument exceeds 62° C., the temperature of the portion in contact with the body becomes higher than 42° C., which may cause a low temperature burn. Therefore, it is preferable to structure the treatment instrument so that the highest temperature is less than 62° C., more preferably less than 55° C., further preferably less than 50° C. Further, in view of the hemorrhoid relieving effect, the maintaining time is preferably not less than four hours, more preferably not less than six hours, further preferably not less than eight hours.

Outer Bag

The outer bag is formed of a non-air-permeable material, such as a synthetic resin, including nylon, polyethylene, polypropylene and the like.

Adhesive and Backing Film

The adhesive 3, the backing film and the backing sheet 4 may be selected from any known adhesives, films and sheets. The adhesive 3 is preferably formed of a material that does not cause skin trouble when the treatment instrument is directly attached to the skin.

Usage

Figure 4:
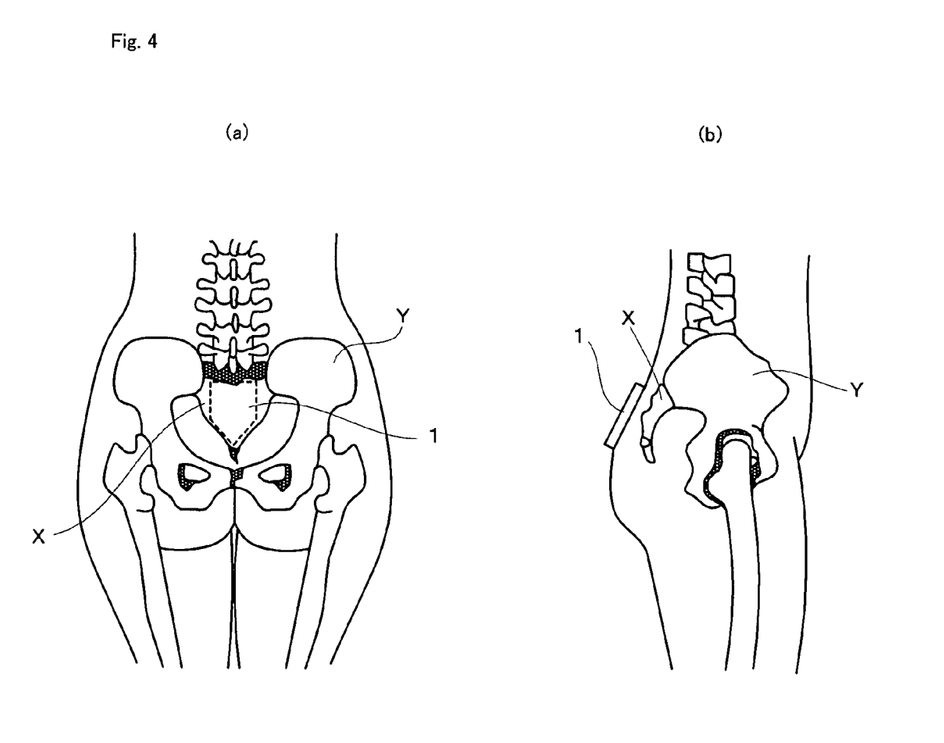
FIG. 4 A plan view illustrating the treatment instrument of FIG. 1 in use.

The following explains the usage of the treatment instrument having the above structure. When the container 1 is covered with a backing film or a backing sheet 4, the backing film or the backing sheet 4 is peeled off from the container 1. Thereafter, as shown in FIG. 4, the adhesive side of the treatment instrument is attached to the back of the user over the sacrum X and/or the skin in its periphery. The treatment instrument may be adhered either directly to the skin or indirectly through clothing.

The treatment using this instrument is preferably performed by adhering the treatment instrument having the above structure to the patient's body at a frequency of 1 to 6 times a day, 4 to 10 hours each at a time.

Effect

By thus adhering the treatment instrument heated by the heat generating material 2 onto the sacrum X and/or the skin in its periphery, the blood circulation in the entire pelvis Y is facilitated. This presumably relieves symptoms of hemorrhoids, particularly external hemorrhoids and internal hemorrhoids. More specifically, the thermal effect relieves the pain and/or itchiness of hemorrhoids, and also reduces the hemorrhoid. Moreover, since the peripheral area of the sacrum X is warmed, an effect of relieving constipation is provided, thereby preventing the discharge of hard feces. This can further facilitate recovery from hemorrhoids.

As such, unlike the conventional technique of inserting a treatment instrument into the patient's body, the present embodiment can relieve the symptoms of hemorrhoids by directly or indirectly adhering a treatment instrument to the sacrum X and/or the skin in its periphery of the patient. With such an instrument, the present embodiment has advantages of easy attachment to the body and comfort in use.

[Example]

An example of the present invention is described below. However, the present invention is not limited to the example.

The treatment instrument in the present example is formed of the following materials.

Container

A pentagon container, similar to the container shown in FIG. 1, was used.

(1) Front Sheet

The front sheet was formed by laminating a nonwoven fabric (basis weight=30 g/m²) produced by the span lace method using polyethylene terephthalate on a porous film formed of a polyethylene film (70 μm).

(2) Rear Sheet

The rear sheet was formed of a polyethylene film (60 μm).

(3) Adhesive

A hot-melt adhesive was applied onto the rear sheet (2) with a thickness of 30 μm.

Heat Generating Material

The content of the heat generating material in the container was changed depending on the container size. However, all heat generating materials had the following composition.

Iron powder 55%
Activated carbon 13%
Metal salt 1%
Water 26%
Vermiculite 3%
Sodium polyacrylate 2%

The amounts of the heat generating materials were 3 g, 6 g, 10 g, 12 g, 15 g, 25 g, 30 g, 35 g, 38 g, 40 g, 45 g and 50 g, respectively for the container areas of 15 cm$^2$, 28.5 cm$^2$, 45 cm$^2$, 50 cm$^2$, 67 cm$^2$, 74 cm$^2$, 85 cm$^2$, 91 cm$^2$, 117 cm$^2$, 124 cm$^2$, 143 cm$^2$ and 156 cm$^2$.

With these materials, multiple treatment instruments were made, and the following tests were carried out to evaluate the effects of these instruments. In the multiple treatment instruments used in the following tests, the area of the container, air permeability, and the amount of the heat generating material were varied. However, the materials and their compositions were the same.

1. Warmth 169 instrument samples with variable container areas (area in a plan view) and variable air permeabilities were prepared. 10 healthy test subjects used these samples to evaluate the warmth of the instruments. The test subjects wore the treatment instruments over underwear so that the instruments were positioned in the vicinity of the sacrum. The air permeability was determined based on the water vapor transmission rate measured by method A (humidity sensor method) as defined by JIS K7129. The test subjects evaluated the instruments as to whether they had satisfactory warmth, i.e., the instrument was not excessively hot but sufficiently warm. Table 1 shows the results.

TABLE 1

| g/m$^2$/day | | | | | | | | | | | | |
|---|---|---|---|---|---|---|---|---|---|---|---|---|
| 471 | C | C | C | C | C | C | C | C | C | C | C | C |
| 422 | C | C | C | C | C | C | C | C | C | C | C | C |
| 413 | C | B | B | B | B | B | B | B | B | C | C | C |
| 390 | C | B | A | A | A | A | A | A | A | B | C | C |
| 378 | C | B | A | A | A | A | A | A | A | B | B | C |
| 332 | C | B | A | A | A | A | A | A | A | A | B | C |
| 294 | C | B | A | A | A | A | A | A | A | A | B | C |
| 274 | C | B | A | A | A | A | A | A | A | A | B | C |
| 265 | C | B | A | A | A | A | A | A | A | A | B | C |
| 252 | C | B | A | A | A | A | A | A | A | A | B | C |
| 234 | C | B | A | A | A | A | A | A | A | A | B | C |
| 214 | C | B | B | B | B | B | B | B | B | B | A | C |
| 198 | C | C | C | C | C | C | C | C | C | C | C | C |
|  | 15 | 28.5 | 45 | 50 | 67 | 74 | 85 | 91 | 117 | 124 | 143 | 158 cm$^2$ |

A: 7 or more people were satisfied
B: 5 to 6 people were satisfied
C: 4 or less people were satisfied The results showed that the instrument had insufficient warmth when the area was less than 28.5 cm$^2$, and became excessively hot when the area was greater than 143 cm$^2$. The results also showed that the instrument became excessively hot when the air permeability was greater than 422 g/m$^2$/day, and that the warmth generated was insufficient when the air permeability was less than 214 g/m$^2$/day.

Another test regarding heat generation of the treatment instrument was performed as detailed below.

Figure 5:
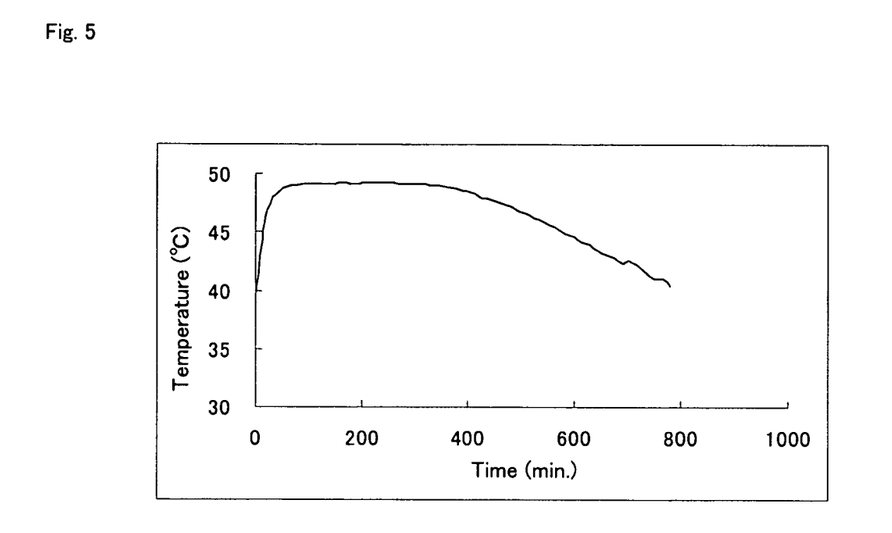
FIG. 5 A graph showing the results of a temperature measurement test using the example of the present invention.

(1) A temperature measurement test was performed according to JIS 4100 with respect to a treatment instrument having an area of 67 cm$^2$ and an air permeability of 378 g/m$^2$/day. FIG. 5 shows the results. The highest temperature was 49° C., the maintaining time was 13 hours, the temperature rise was 8 minutes, and the temperature guarantee time was 76%.

Figure 6:
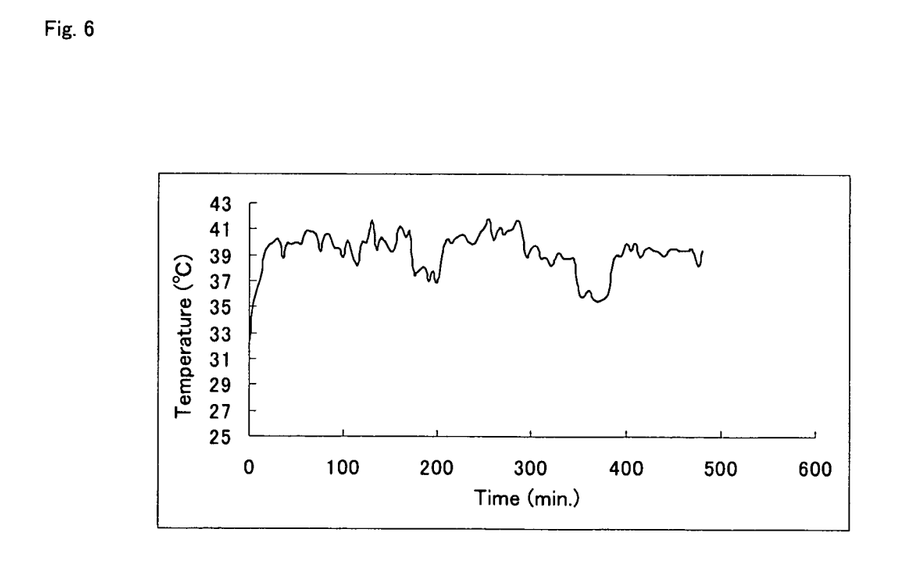
FIG. 6 A graph showing the results of a skin temperature measurement test using the example of the present invention.

(2) The treatment instrument used in the test (1) was adhered to the test subject's body through clothing. The temperature of the skin was measured using a thermo recorder (model RT-12, produced by ESPEC MIC Corp.). FIG. 6 shows the results. The temperature of the skin did not exceed 42° C. Accordingly, the instrument had no risk of causing a low temperature burn.

2. Uncomfortable Feeling 13 treatment instrument samples with varying areas were prepared. All samples had an air permeability of 378 g/m$^2$/day. 10 healthy test subjects used the samples to examine whether they had an uncomfortable feeling when they put on the instrument. Table 2 shows the results.

TABLE 2

| Area (cm$^2$) | | | | | | | | | | | |
|---|---|---|---|---|---|---|---|---|---|---|---|
| | 15 | 28.5 | 45 | 50 | 67 | 74 | 85 | 91 | 117 | 124 | 143 | 156 |
| Evaluation | A | A | A | A | A | A | A | A | B | C | C | C |

A: 7 or more people were satisfied
B: 5 to 6 people were satisfied
C: 4 or less people were satisfied According to the results, the test subjects felt uncomfortable when the area was greater than 117 cm$^2$. Many of the test subjects felt that the instruments of these sizes were bulky and came off easily.

3. Hemorrhoid Relieving Effect

The warming and pain relieving effects were examined with four hemorrhoid patients, using 9 treatment instrument samples with variable air permeabilities and areas. Table 3 shows the results.

TABLE 3

| | 1 | 2 | 3 | 4 | 5 | 6 | 7 | 8 | 9 | 10 | 11 |
|---|---|---|---|---|---|---|---|---|---|---|---|
| Air Permeability (g/m$^2$/day) | 274 | 378 | 332 | 214 | 413 | 214 | 378 | 198 | 198 | 471 | 378 |
| Area (cm$^2$) | 45 | 67 | 91 | 45 | 67 | 91 | 15 | 45 | 67 | 91 | 156 |
| Warmth | A | A | A | B | B | B | C | C | C | C | C |
| Pain relieving effect | A | A | A | B | B | B | C | C | C | C | C |

A: 4 people were satisfied
B: 3 people were satisfied
C: 2 people or less were satisfied As shown above, good results were obtained for treatment instruments 1 to 6. Particularly, the results suggested a correlation between the pain relieving effect and warmth.

Another test was performed for further evaluation using a treatment instrument having an air permeability of 378 g/m$^2$/day and a container area of 50 cm$^2$. The following are details of the test subjects, who were all women.

TABLE 4

| | Age | Type of hemorrhoid | Severity | History for hemorrhoids |
|---|---|---|---|---|
| 1 | 60-69 | Internal hemorrhoids (Class 2) | Middle (pain) | 1 year or more |
| 2 | 20-29 | Internal hemorrhoids (Class 2) | Mild (pain) | 1 year or more |
| 3 | 40-49 | Internal hemorrhoids (Class 2) | Mild (pain) | Two weeks |
| 4 | 30-39 | Internal hemorrhoids (Class 1) | Mild (pain) | 1 year or more |
| 5 | 50-59 | Internal hemorrhoids (Class 1) | Mild (pain) | 1 year or more |
| 6 | 30-39 | Anal fissure | Mild (pain) | 1 month or less |
| 7 | 20-29 | Internal hemorrhoids (Class 2) | Mild (pain) | 1 year or more |
| 8 | 40-49 | Internal hemorrhoids (Class 1) | Mild (swelling) | 1 year or more |
| 9 | 30-39 | Internal hemorrhoids (Class 1) | Mild (pain) | Two weeks |

TABLE 4-continued

| | Age | Type of hemorrhoid | Severity | History for hemorrhoids |
|---|---|---|---|---|
| 10 | 30-39 | Internal hemorrhoids (Class 1) | Mild (pain) | 1 year or more |

TABLE 4-continued

| | Age | Type of hemorrhoid | Severity | History for hemorrhoids |
|---|---|---|---|---|
| 11 | 30-39 | Internal hemorrhoids (Class 1) | Mild (pain) | 6 months or less |

Each test subject wore the treatment instrument every morning (once a day) over their underwear so that the treatment instrument was positioned in the vicinity of the sacrum. The test was continued for three days, with the following results.

(1) Overall Satisfaction Level
Satisfied: 9%
Satisfied somewhat: 82%
Neither satisfied nor unsatisfied: 9%
Unsatisfied somewhat: 0%
Unsatisfied: 0%

(2) Effect

The test subjects who chose either "Satisfied" or "Satisfied somewhat" were surveyed in more detail regarding the effects.

TABLE 5

| Relief of pain | 7 people |
|---|---|
| Relief of swelling | 2 people |
| Reduction of hemorrhoid | 1 person |
| Relief of constipation | 1 person |
| Relief of lumbar pain | 1 person |

4. The Body Part where the Treatment Instrument is Applied

Still another test was performed with four hemorrhoid patients, using a treatment instrument having an air permeability of 378 g/m²/day and an area of 67 cm². In this test, each patient put on the treatment instrument over underwear in the vicinity of the anus so that the instrument directly warmed the anus.

After eight hours from the application, warmth, feel of use, and the hemorrhoid relieving effect were evaluated.

TABLE 6

| Warmth | Feel of use | Hemorrhoid relieving effect |
|---|---|---|
| A | C | C |

A: 4 people were satisfied
B: 3 people were satisfied
C: 0 people were satisfied According to the results, the warmth was satisfactory; however, no effect of relieving hemorrhoids was observed. Although the details were not clarified, this is presumably because the flesh of the buttocks blocked heat transfer from the instrument to the affected part, or because, even though the heat was transferred, the heating of the anus was not effective for relieving hemorrhoids. In comparison with the test 3, this result suggested that heating in the vicinity of the sacrum or the skin in its periphery is effective to prevent or treat hemorrhoids.

The invention claimed is:

1. A method for preventing or treating hemorrhoids, comprising the step of:
preparing an instrument for preventing or treating hemorrhoids, comprising a container having air permeability and being adhered to a patient's back in contact with the skin over at least one of the sacrum and/or its periphery either directly to the skin or indirectly through clothing; and a heat generating material which generates heat by oxidation upon contact with air and is contained in the container; and
adhering the instrument to a back of a hemorrhoid patient or a user trying to prevent hemorrhoids in contact with the skin over at least one of the sacrum and its periphery either directly to the skin or indirectly through clothing,
wherein the container substantially has a pentagonal shape in a plan view provided with a substantially triangle-shaped projecting portion on one end, the area of the container in a plan view is in a range of from 45 to 117 cm², and
the container has an air permeability of from 234 to 390 g/m²/day.

2. The method according to claim 1, wherein the container comprises an irregular thickness.

3. The method according to claim 1, wherein a degree of heat-generation per unit area is at least 45 cal/cm².

4. The method according to claim 1, wherein the container comprises a slit in the substantially triangle-shaped projecting portion so that the substantially triangle-shaped projecting portion is divided into two portions.

* * * * *